United States Patent [19]
Fore

[11] Patent Number: 4,989,612
[45] Date of Patent: * Feb. 5, 1991

[54] RESPIRATION MONITOR

[75] Inventor: Don C. Fore, Vinita, Okla.

[73] Assignees: William H. Castor, Vinita; Ida F. Thrope, Spavinaw, both of Okla.

[*] Notice: The portion of the term of this patent subsequent to Jun. 13, 2006 has been disclaimed.

[21] Appl. No.: 275,770

[22] Filed: Nov. 23, 1988

Related U.S. Application Data

[63] Continuation-in-part of Ser. No. 48,896, May 12, 1987, Pat. No. 4,838,279.

[51] Int. Cl.$^5$ ............................................... A61B 5/08
[52] U.S. Cl. ...................................... 128/721; 128/782
[58] Field of Search ............... 128/716, 719, 720, 721, 128/739, 774, 782

[56] References Cited

U.S. PATENT DOCUMENTS

| | | | |
|---|---|---|---|
| 3,097,639 | 7/1963 | Streimer | 128/721 |
| 3,517,999 | 6/1970 | Weaver | 128/721 |
| 4,279,257 | 7/1981 | Hochstein | 128/722 |
| 4,392,126 | 7/1983 | Lojala | 128/782 |
| 4,664,129 | 5/1987 | Helzel et al. | 128/721 |
| 4,838,279 | 6/1989 | Fore | 128/721 |
| 4,846,462 | 7/1989 | Regnier et al. | 128/721 |

FOREIGN PATENT DOCUMENTS

0093545 11/1983 European Pat. Off. ............ 128/721

Primary Examiner—Randall L. Green
Assistant Examiner—K. M. Reichle
Attorney, Agent, or Firm—Dunlap, Codding, Peterson & Lee

[57] ABSTRACT

A monitor for monitoring motion wherein a light source is positioned a distance from a light conductor and the distance between the light source and the light conductor is varied in response to motion. The light received by the light conductor is used to provide output indications indicative of the monitored motion.

12 Claims, 7 Drawing Sheets

RESPIRATION MONITOR

CROSS-REFERENCE TO RELATED APPLICATIONS

The present application is a continuation-in-part of Applicant's patent application entitled: Respiration Monitor; Ser. No. 048,896; filed May 12, 1987, now U.S. Pat. No. 4,838,279 the disclosure of this co-pending application hereby specifically is incorporated herein by reference.

FIELD OF THE INVENTION

The present invention relates generally to monitors and, more particularly, but not by way of limitation, to a monitor having a light emitting source and a receiving light conductor which are spaced a predetermined distance apart which distance varies in response to motion of an individual or a monitor having a sending and a receiving light conductor spaced a predetermined distance from a mirror wherein the distance between the ends of the receiving and sending light conductors and the mirror varies in response to motion of an individual.

BRIEF DESCRIPTION OF THE DRAWINGS

FIG. 4A and 4B comprise a schematic view showing a portion of the respiration monitoring control diagrammatically shown in FIG. 1.

FIG. 10 is a schematic view showing another embodiment of a respiration monitoring control.

FIG. 11 is a sectional view of a modified detector housing.

DESCRIPTION OF THE PREFERRED EMBODIMENTS

Figure 1:
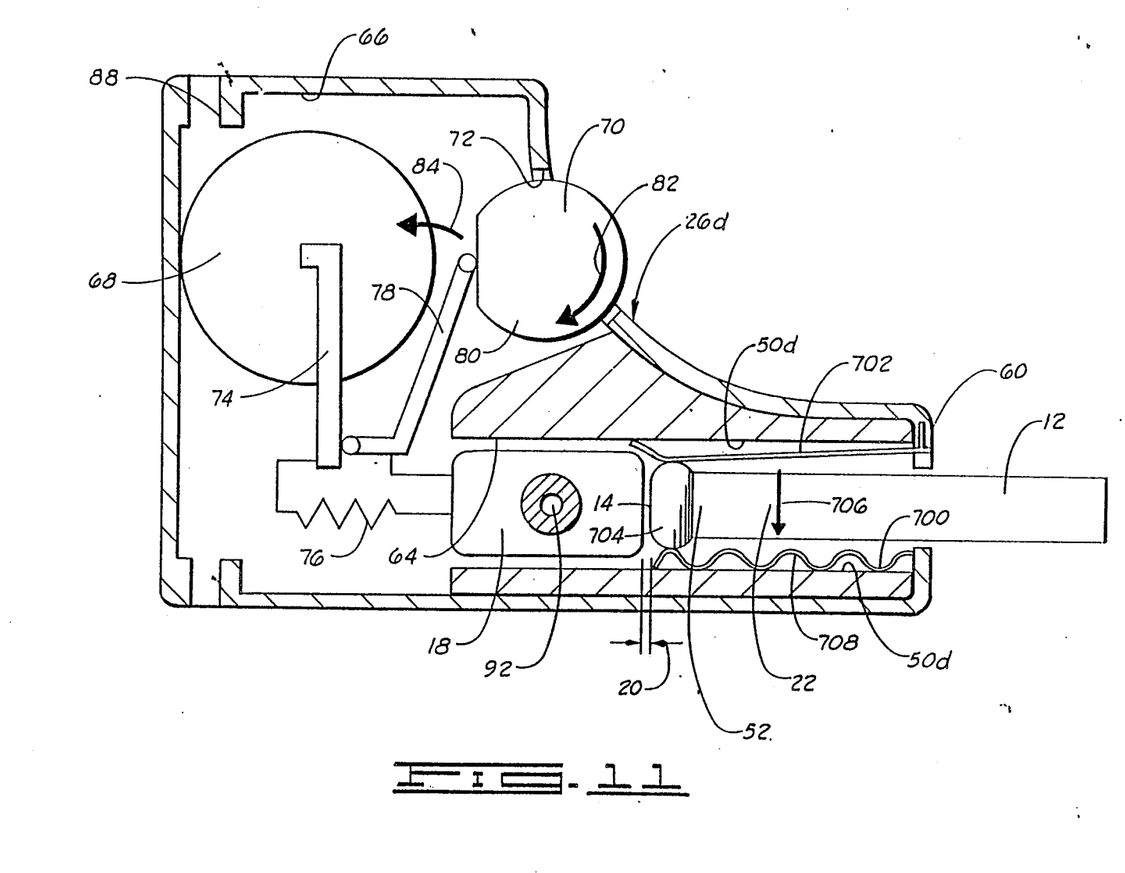
FIG. 1 is a diagrammatic, partial elevational, partial sectional view of a respiration monitor constructed in accordance with the present invention.

Diagrammatically shown in FIG. 1 is a respiration monitor which is constructed in accordance with the present invention and designated by the general reference numeral 10. The respiration monitor 10 includes a receiving light conductor 12 having a receiving end 14 and a sending end 16 and a light source 18 which is positioned near and spaced a distance 20 from the receiving end 14 of the receiving light conductor 12. The light source 18 is constructed and adapted to emit light and the receiving light conductor 12 is constructed and adapted to receive light from the light source 18 at the receiving end 14 and to conduct light between the receiving and the sending ends 14 and 16, respectfully, the receiving light conductor 12 being more particularly a fiber optic 22 with a plastic shield 24 disposed generally about the fiber optic 22. The respiration monitor 10 also includes a detector housing 26 and a strap assembly 28.

The receiving end 14 of the receiving light conductor 12 is movably insertable and disposed in a portion of the detector housing 26. The detector housing 26 is adapted to receive the receiving end 14 of the receiving light conductor 12 and to hold and support the portions of the receiving light conductor 12 insertable therein in a position wherein the receiving end 14 of the receiving light conductor 12 is spaced the distance 20 from the light source 18. The detector housing 26 also is adapted to support the light source 18 disposed the predetermined distance 20 from the receiving end 14 of the receiving light conductor 12. The receiving end 14 of the receiving light conductor 12 is movably supported in the detector housing 26 so that the distance 20 between the receiving end 14 of the receiving light conductor 12 and the light source 18 varies in response to respiration motion of the individual being monitored in a manner and for reasons which will be made more apparent below.

The sending end 16 of the receiving light conductor 12 is connected to a respiration monitoring control 30. The respiration monitoring control 30 is adapted and constructed to receive light emitted from the sending end 16 of the receiving light conductor 12 and to provide output indications indicative of respiration motion.

In general, the respiration monitor 10 of the present invention particularly is constructed to monitor respiration motion of an individual and to provide output indications indicative of respiration motion. In one preferred embodiment, the respiration monitoring 30 is adapted to provide an output indication indicative of a cessation or absence of respiration for a predetermined period of time, apnea. The strap assembly 28 is removably connectable to a portion of the individual which moves in response to respiration motion of the individual. Preferably, the strap assembly is adapted to be strapped about an individual's chest or abdomen for example.

In operation, light is emitted from the light source 18 across the distance 20 between the receiving end 14 of the receiving light conductor 12 and the light source 18 and the light is received at the receiving end 14 of the receiving light conductor 12. The received light is conducted by the receiving light conductor 12 generally between the receiving end 14 and the sending end 16 thereof. The received light is emitted at the sending end 16 of the receiving light conductor 12 and the light emitted from the sending end 16 of the receiving light conductor 12 is received at or inputted into the respiration monitoring control 30.

During respiration (inhaling and exhaling), the strap assembly 28 is expanded and contracted periodically in response to the respiration motion and the expansion of the strap assembly causes the distance 20 between the receiving end 14 of the receiving light conductor 12 and the light source 18 to be increased, while contraction of the strap assembly 28 causes the distance 20 to be decreased. An increase in the distance 20 results in a decrease in the intensity of light conducted between the receiving end 14 and the sending end 16 of the receiving light conductor 12 and a reduction or decreasing of the distance 20 results in an increase in the intensity of light conducted between the receiving end 14 and the sending end 16 of the receiving light conductor 12. The respiration monitor control 30, more particularly, is adapted to receive light from the sending end 16 of the receiving light conductor 12 and to provide output indications indicative of respiration motion in response to determining indications of respiration motion indicated by changes in the intensity of light received from the sending end 16 of the receiving light conductor 12. In other words, periodic increase and decrease in the distance 20 results in periodic increase and decrease in the intensity of light received by the respiration monitoring control 30 and this periodic increasing and decreasing in the intensity of light received by the respiration monitoring control 30 provides the means for determining respiration motion.

Figures 1, 2, 3:
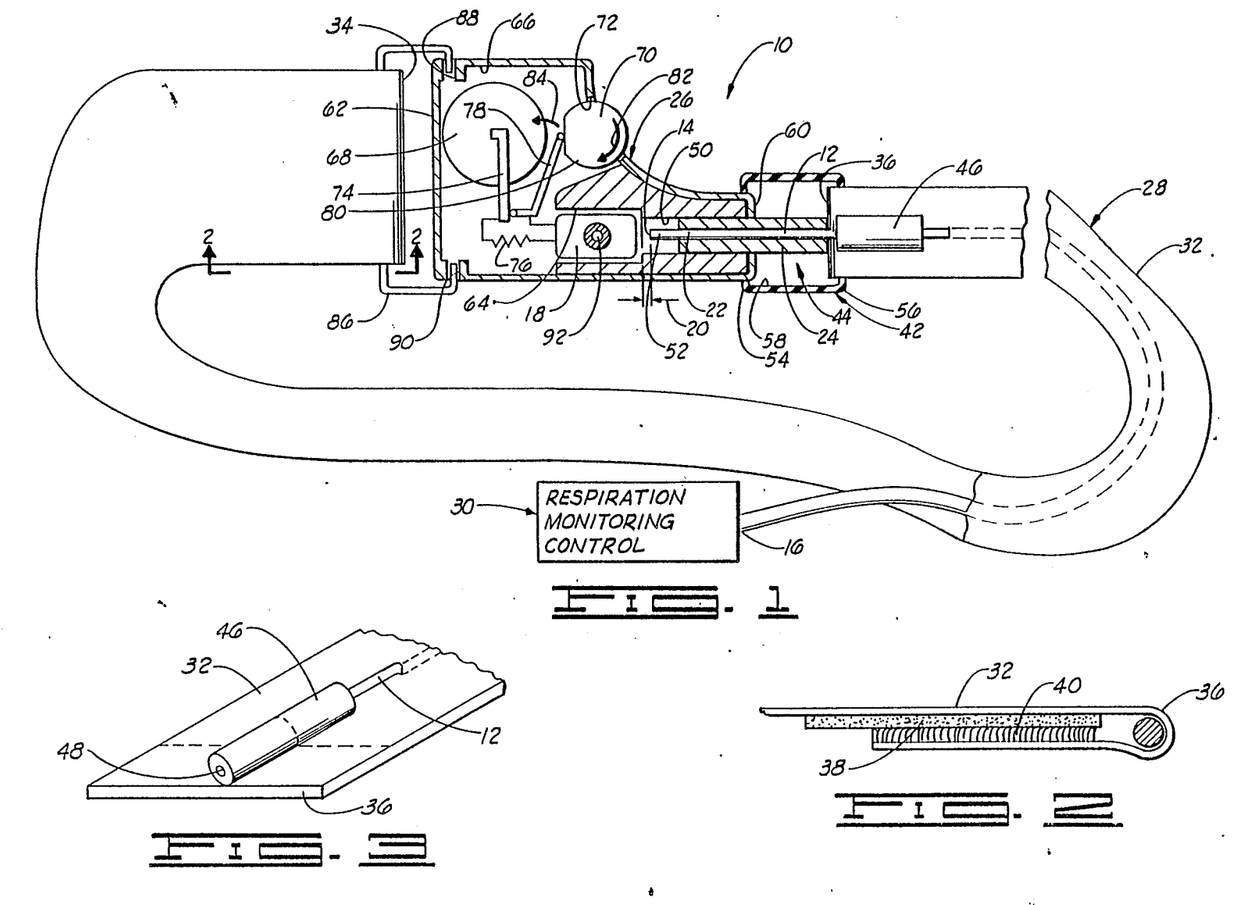
FIG. 2 is a side elevational view, partial sectional view of a portion of the respiration monitor of FIG. 1, taken substantially along the lines 2—2 of FIG. 1.
FIG. 3 is a partial perspective, fragmentary view of a portion of the respiration monitor of FIG. 1 showing the connection of the receiving light conductor to a portion of the strap assembly.

As shown in FIG. 2, the strap assembly 28 comprises a strap 32 having opposite ends 34 and 36. A strip of connecting material 38 is secured to a portion of one side of the strap 32 generally near the end 34 thereof and another strip of connecting material 40 is secured to one side of the strap 32 generally near the end 34 thereof and spaced a distance from the connecting material 38. The connecting material 38 is spaced a distance from the end 34 and the connecting material 40 is disposed generally near and adjacent the end 34 of the strap 32. The connecting materials 38 and 40 maybe materials such as Velcro, for example. The connecting materials 38 and 40 are positioned on the strap 32 so that, when the strap 32 is extended about an individual, the end 34 of the strap 32 may be adjustably moved through a portion of the detector housing 26 to adjust of the length of the strap 32 to fit the individual and then the connecting portions 38 and 40 can be pressed into contacting engagement for securing the end 34 to the detector housing 26. The end 36 of the strap 32 is movably connected to the detector housing 26 so that the portion of the strap 32 generally near the end 36 moves in response to respiration motion with respect to the detector housing 26 for reasons which will be made more apparent below.

More particularly, the end 36 of the strap 32 is connected to the detector housing 26 by way of a flexible connector 42. The flexible connector 42 is constructed and adapted to be stretched and returned to its relaxed condition in response to respiration motion. In one example, the flexible connector 42 was constructed of a thin latex tubing which encompass and encloses a space 44 generally between the end 36 of the strap 32 and the detector housing 26.

The strap 32, except for the flexible connector 42, is constructed of a flexible, non-elastic or virtually non-expandable type of material. The strap 32, except for the flexible connector 42, is constructed of two strips of material with one strip of material being stitched to the other strip of material so that an opening extends between the two strips of material and about the strap 32, the opening being enclosed by the two strip pieces which are stitched together. The receiving light conductor 12 extends through the opening in the strap 32 and extends a distance generally about a portion of the strap 32 with one end portion of the receiving light conductor 12 exiting from the opening in the strap 32 generally near and spaced a distance from the end 36 of the strap 32 and with a portion of the receiving light conductor 12 exiting at a point generally between the ends 34 and 36 of the strap 32 and terminating with the sending end 16 of the receiving light conductor 12 which is connected to the respiration monitoring monitor 30.

A cylindrically shaped tube 46 is secured to the strap 32 generally near the end 36 thereof. The tube 46 has an opening 48 (shown in FIG. 3) which is sized to receive the receiving light conductor 12. The receiving light conductor 12 exits from the opening 48 in the strap 32 and is inserted through the opening 48 in the tube 46.

The receiving light conductor 12 exits from the opening 48 in the tube 46 and is slidably or movably inserted through a light opening 50 formed through one end of the detector housing 26. The receiving light conductor 12 extends a distance through the light opening 50 in the detector housing 26 terminating with the receiving end 14 of the receiving light conductor 12.

As shown in FIG. 1, a portion of the plastic shield 24 generally near the receiving end 14 of the receiving light conductor 12 is removed so that the fiber optic 22 portion of the receiving light conductor 12 extends into the light opening 50 terminating with the receiving end 14 which is disposed generally near and spaced the distance 20 from the light source 18. The exposed fiber optic 22 generally near the receiving end 14 sometimes is referred to herein as an exposed lead portion 52 of the receiving light conductor 12.

The flexible connector 42 has opposite ends 54 and 56 and an opening 58 which extends therethrough intersecting the opposite ends 54 and 56. The end 54 of the flexible connector 52 is secured to the detector housing 26 and the end 56 of the flexible connector 42 is secured to the end 36 of the strap 32.

The receiving light conductor 12 extends through the opening 58 in the flexible connector 42. The flexible connector 42 extends generally about a portion of the detector housing 26 and about a portion of the end 36 of the strap 32 with a portion of the flexible connector 42 extending over and being secured to a portion of the outer peripheral surface of the tube 46. The dashed line in FIG. 3 indicates where a portion of the flexible connector 42 extends over the strap 32 and over the tube 46.

The flexible connector 42 thus encompasses the space 44 extending between the end 36 of the strap 32 and one end of the detector housing 26. The flexible connector 42 is constructed of an opaque material for preventing light from entering into the space 44 and into the light opening 50 in the detector housing 26.

As shown in FIG. 1, the detector housing 26 is generally rectangularly shaped and has opposite ends 60 and 62. The light opening 50, more particularly, is formed through the end 60 of the detector housing 26. A light source opening 64 is formed in the detector housing 26 and the light source opening 64 intersects the light opening 50. The light source opening 64 is sized and adapted to receive the light source 18 which is disposed and supported in the light source opening 64 of the detector housing 26.

A component opening 66 is formed in a portion of the detector housing 26. The component opening 66 is sized and adapted to receive some of the components of the respiration monitor 10, as will be described in greater detail below.

A battery 68 is disposed in the component opening 66 and a portion of an on-off knob 70 is disposed in the component opening 66 of the detector housing 26 with a portion of the on-off knob 70 exiting through an opening 72 in the detector housing 26 so that a portion of the on-off knob 70 is accessible from the exterior of the detector housing 26.

One end of a contact 74 is connected to the battery 68, and the contact 74 extends a distance from the battery 68. The end of the contact 74, opposite the end connected to the battery 68, is connected to the light source 18 by way of a resistor 76.

Another contactor 78 is movably supported in the detector housing 26. In the position shown in FIG. 1, one end of the contactor 78 is in engagement with the contactor 74 thereby establishing electrical continuity between the contactor 74 and 78. The contactor 78 is connected to the light source 18. Thus, when the contactor 78 engages the contactor 74, electrical continuity is established between the battery 68 and the light source 18 thereby energizing the light source 18 and causing the light source 18 to emit light.

The on-off knob 70 has a outer peripheral cam surface 80. The on-off knob 70 is positioned so that the cam surface 80 engages one end of the contactor 78. When the on-off knob 70 is rotated in a direction 82, the cam surface 80 engages one end of the contactor 78 thereby pivoting the contactor 78 in a direction 84 for moving the contactor 78 output of engagement with the contactor 74 and interrupting electrical continuity between the battery 68 and the light source 18.

It should be noted that the battery 68 could be connected to the light source 18 by way of push-button type of on-off switch in lieu of the contactors 74 and 78 and the on-off knob 70.

A U-shaped strap bar 86 is pivotally connected to the end 62 of the detector housing 26. More particularly, one end of the strap bar 86 is pivotally disposed in an opening 88 in one side of the detector housing 26 generally adjacent the end 62 and the opposite end of the strap bar 86 is pivotally disposed in an opening 90 formed in one side of the detector housing 26 generally adjacent the end 62 thereof.

The end 34 of the strap 32 is disposed through the opening between the strap bar 86 and the end 62 of the detector housing 26 and a length of the strap 32 generally near the end 34 thereof is pulled through the opening between the strap bar 86 and the detector housing 26 until the total length of the strap 32 has been adjusted for a particular patient. Then, the connecting material 40 is removably connected to the connecting material 38 to secure the strap 32 connected to the strap bar 86 thereby connecting the end 34 of the strap 32 to the end 62 of the detector housing 26.

As diagrammatically shown in FIG. 1, a small inspection opening 92 is formed through an upper surface of a detector housing 26 generally above the light source 18 to provide a means for visually inspecting the detector housing 26 to assure that the light source 18 is emitting light.

In operation, the end 34 of the strap 32 is disconnected from the strap bar 86 and the strap 32 with the detector housing 26 connected thereto is strapped about the individual. Then, the end 34 of the strap 32 is adjustably connected to the strap bar 86 to secure the strap 32 with the detector housing 26 connected thereto about a portion of an individual which moves in response to respiration motion. The on-off knob 70 is rotated in a direction opposite the direction 82 to move the contactor 78 into engagement with contactor 74 thereby establishing electrical continuity between the battery 68 and the light source 18 for causing the light source 18 to emit light.

Light emitted from the light source 18 is received by the receiving end 14 of the receiving light conductor 12 and the receiving light conductor 12 conducts the received light generally between the receiving end 14 and the sending end 16. The light is emitted from the sending end 16 and received by the respiration monitoring control 30.

As the individual inhales and exhales, the flexible connector 42 portion of the strap assembly 28 expands and contracts, thereby increasing and decreasing the distance 20 between the light source 18 and the receiving end 14 of the receiving light conductor 12. The increasing of the distance 20 between the receiving end 14 of the receiving light conductor 12 and the light source 18 results in a decrease in the intensity of light received by the receiving end 14 of the receiving light conductor 12, thereby resulting in a decrease in the intensity of light received by the respiration monitoring control 30 from the sending end 16 of the receiving light conductor 12. As the individual exhales, the flexible connector 42 portion of the strap assembly 28 contracts thereby decreasing the distance 20 between the light source 18 in the receiving end 14 of the receiving light conductor 12 resulting in an increase in the intensity of light received by the receiving end 14 of the receiving light conductor 12 and an increase in the intensity of the light emitted from the sending end 16 of the receiving light conductor 12 and received by the respiration monitoring control 30.

The respiration monitoring control 30 receives light from the sending end 16 of the receiving light conductor 12 and is constructed and adapted to detected respiration motion by detecting periodic increases and decreases in the intensity of light received from the sending end 16 of the receiving light conductor 12. More particularly, the respiration monitor control 30 is constructed and adapted to provide an alarm signal indicating the cessasion or absence of respiration motion (apnea) in response to detecting virtually no change in the intensity of light received from the sending end 16 of the receiving light conductor 12 for a predetermined period of time, such alarm signal being received by an alarm for providing perceivable output indications in response to receiving such an alarm signal.

The receiving light conductor 12 comprises what is commonly referred to in the industry as a fiber optic with a plastic shield. Fiber optics are well known in the art and a detailed description of the construction and operation of such fiber optics is not deemed necessary herein.

Figure 5:
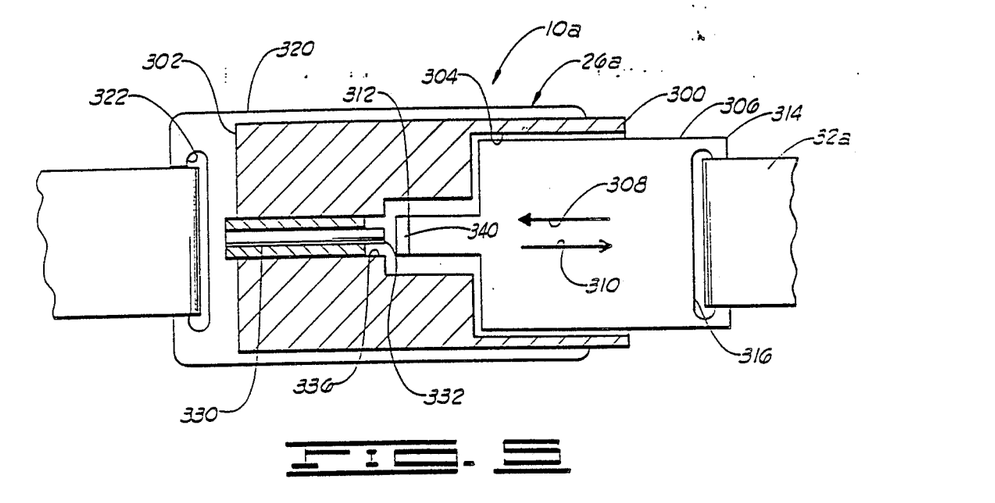
FIG. 5 is a sectional view, partial elevational view of a modified respiration monitor which is constructed in accordance with the present invention.
Figure 6:
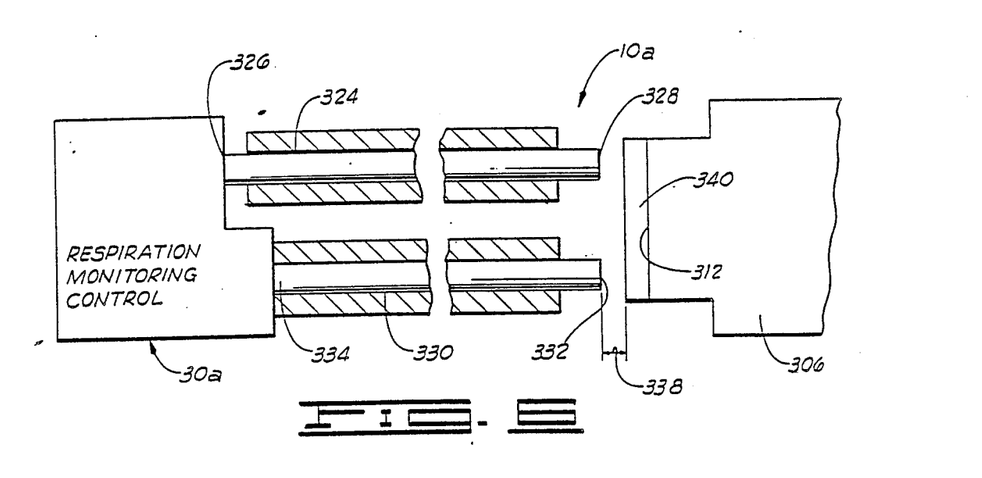
FIG. 6 is a sectional view, partial elevational view, partial diagrammatic view of the modified respiration monitor shown in FIG. 5.

It should be noted that the terms "receiving" and "sending" as well as the terms "sending end" and "receiving end" as used in conjunction with the receiving light conductor 12 or as used later herein with respect to the light conductors shown in FIGS. 5 and 6 are merely for reference and are not intended to described structural differences in the end of the light conductors described herein.

Figure 4A:
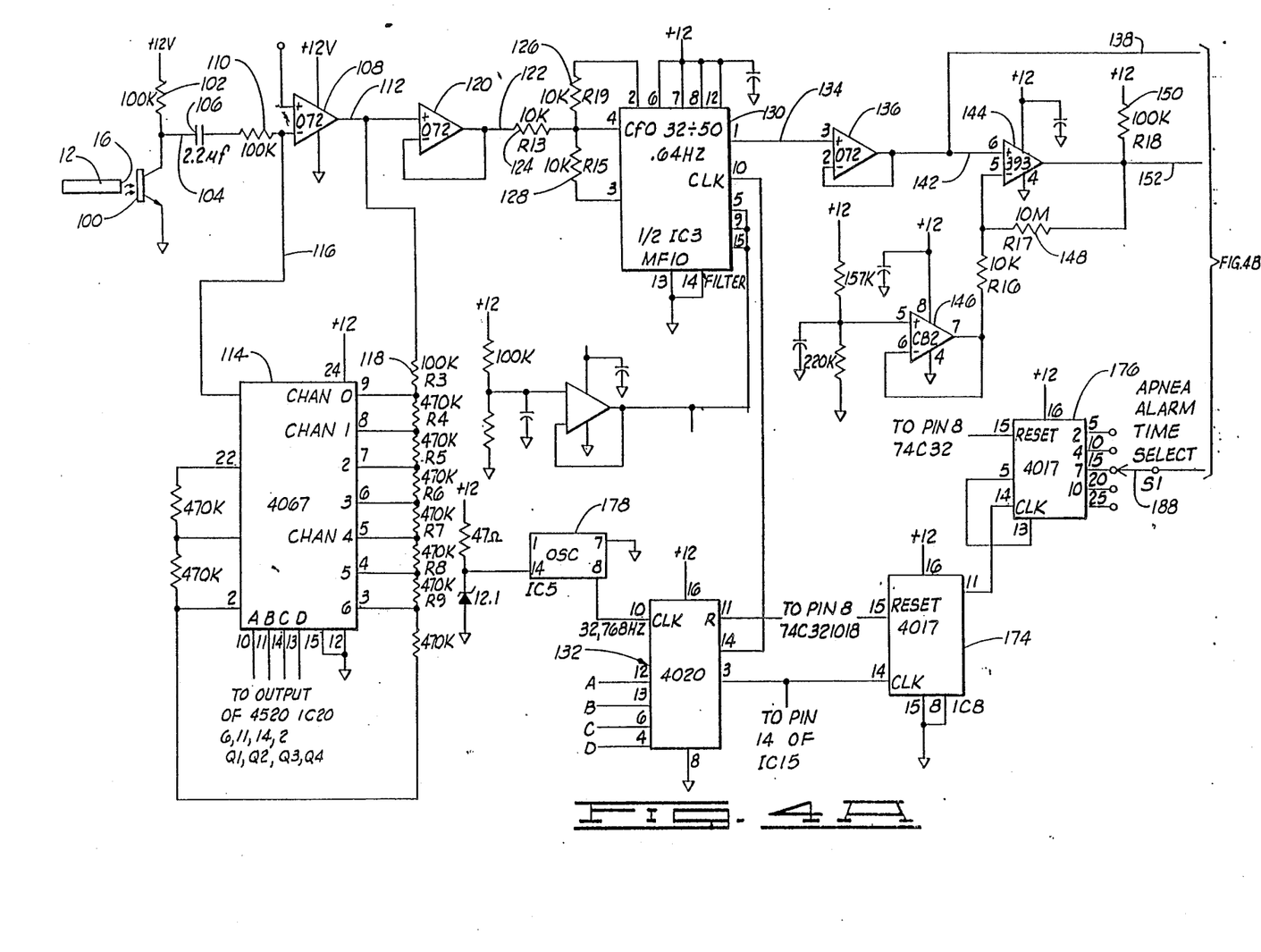

The respiration monitoring control 30 converts the light received from the sending end 16 of the receiving light conductor 12 into an electrical signal in an analog format indicative of the intensity of light received at the receiving end 14 of the receiving light conductor 12 or, in other words, indicative of respiration motion, and the respiration monitoring control 30 determines a cessation or absence of the respiration motion by determining virtually no change in the intensity of light emitted from the sending end 16 of the receiving light conductor 12 for a predetermined period of time, in the respiration monitoring control 30 provides an alarm signal in response to determining a cessation or absence of respiration motion for the predetermined period of time. One embodiment of a portion of the respiration monitoring control 30 for performing the functions just described as shown in greater detail in FIG. 4 (FIGS. 4A and 4B).

As shown in FIG. 4, the sending end 16 of the receiving light conductor 12 is disposed near the base of a phototransistor 100. The phototransistor 100 receives light from the sending end 16 of the receiving light conductor 12 at the base junction, the phototransistor 100 being adapted to conduct in response to receiving light at the base junction thereof. The phototransistor 100 and a resistor 102 form a DC amplifier at the junction of the phototransistor 100 collector and the resistor 102, the amplified signal being conducted over a conductor 104.

A ceramic disc capacitor 106 is interposed in the conductor 104 and the signal from the amplifier formed by the phototransistor 100 and the resistor 102 is passed through the capacitor 106 and the signal on the signal path 104, after being passed through the capacitor 106, no longer is a DC signal, but is an AC signal. The DC component of the signal is blocked by the capacitor 106, but the AC component is passed through the capacitor 106. Only low frequency signals, below about 10 Hz, will pass through the capacitor 106 so that the capacitor 106 not only couples the signal from the amplifier comprising the phototransistor 100 and the resistor 102 to a sense amplifier 108, but also acts as the first stage in electrically filtering the input signal.

The signal outputted through the capacitor 106 is inputted into the sense amplifier 108 through a resistor 110. The signal outputted by the amplifier comprising the phototransistor 100 and the resistor 102 is inputted into the inverting input of the sense amplifier 108 so that the signal outputted by the sense amplifier 108 on a signal path 112 is inverted.

The output from the resistor 110 also is connected to a BCD controlled analog switch 114 by way of a signal path 116. The analog switch 116 controls the gain of and thus the sensitivity of the sense amplifier 108. The analog switch 114 is used as a variable resistor switch and by so using the analog switch 114, the gain of the sense amplifier 108 can be changed by inputting the signal into the analog input of the analog switch 114 and then selecting a path through the analog switch 114 by means of the BCD code that controls the analog transmission gates in the analog switch. For example, with a BCD code of 0000 path number one has been selected through the analog switch 114, so the signal from the resistor 110 present at pin 1 is now passed through transmission gate 1 of the analog switch 114. Transmission gate 1 of the analog switch 114 equals the channel 0. The output of channel 0 is available at pin 9 of the analog switch 114. The signal is now passed through a resistor 118 back to the output of the sense amplifier 108. In this manner, the sense amplifier 108 now has an input resistor of 100 ohms and a feedback resistor of 100,000 ohms and the sense amplifier 108 now has a gain of 1,000. If, for example, the BCD code for channel 6 had been presented to the control inputs, designated A, B, C, D in FIG. 4, then channel 5 would have been selected and the signal present at pin 1 of the analog switch 114 would now pass through the resistors designated in FIG. 4 by the references R7, R6, R5, R4, and R3 before being inputted into the sense amplifier 108.

This would increase the gain of the sense amplifier 108, since the feedback resistor would now be 1,980,000 ohms so that the gain of the sense amplifier now would be 19,800.

The output of the sense amplifier 108 is connected to the non-inverting input of a buffer amplifier 120. The gain of the buffer amplifier 120 is unity.

The buffer amplifier 120 output is provided on a signal path 122 through a resistor 124. The resistor 124 is connected to a pair of resistors 126 and 128. The resistors 124, 126 and 128 control the gain at the input of an active filter 130. The active filter 130 is configured in a low pass mode. A system clock 132 outputs a clock signal which is inputted to the active filter 130 and provides a precision clock signal for the active filter 130. The active filter 130 is configured to pass signals only below 0.65 Hz (approximately 2 cycles per second), and any signal that has a frequency greater than this is rejected by the active filter 130 so that the output of the active filter 130 always is below 0.65 Hz. The output of the active filter 130 is provided on a signal path 134 and the active filter 130 output is inputted into a buffer 136. The buffer 136 output on a signal path 138 is inputted into a ten step bar graph display driver 140 (FIG. 4B).

The output of the buffer 136 provided on a signal path 142 also is inputted into a voltage comparator 144. A 7.09 volt stable reference voltage is outputted by an amplifier 146 which is inputted into the voltage comparator 144. Any signal inputted the voltage comparator 144 by way of the signal path 142 that exceeds the reference voltage (7.09 volts) causes the voltage comparator 142 to swing HIGH (plus 12 volts) from its normally LOW (ground) output. A resistor 148 provides hysteresis to the voltage comparator 144, feeding back approximately 25 millivolts of signal back to the input so that the voltage comparator 144 has a "snap" like action and is made more immune to spurious or noisy signals. A resistor 150 causes the output of the voltage comparator 144 to be definitely HIGH or definitely LOW.

The output of the voltage comparator 144 on a signal path 152 is inputted into a monostable multivibrator 154 (FIG. 4B). The monostable multivibrator 154 is configured in its non-retriggerable mode so that a signal at its input will cause only one signal at its output. For example, the voltage comparator 144 may output a signal one millisecond in duration, the multivibrator 154 will output one signal of a approximately 0.500 milliseconds, and no other signal inputted into the input of the multivibrator 154 will cause the output to go HIGH during this 0.500 millisecond period of time until the lapse of the 0.500 millisecond period. Even if the voltage comparator 144 outputs several signals during the 0.500 millisecond period of time after the monostable multivibrator 154 has been triggered, the output of the multivibrator 154 will be unaffected and the output of the multivibrator 154 will return to a LOW state until its is retriggered. The monostable multivibrator 154 output for "Q" is outputted on a signal path 156 and inputted into a buffer 158, an inverting buffer. The output of the buffer 158 is connected to a light emitting diode 160 through a resistor 162. The light emitting diode 160 provides an output indication indicating that the respiration monitoring control 30 has detected, filtered and compared one breath. When the respiration monitoring 30 circuitry is properly adjusted, the light emitting diode 160 will go "ON" with each breath taken during the monitoring of respiration motion of an individual.

The "Q" output of the monostable multivibrator 154 on the signal path 156 is also inputted into an OR gate 164. The output of the OR gate 164 is connected to the reset inputs of BCD to 7 segment display decoder drivers 166 and 168. The output of the OR gate 164 also is connected to the reset inputs of a frequency divider 170 through an OR gate 172. Frequency dividers 174 and 176 (FIG. 4A) also to the reset of the system clock 132. The output of the OR gate 172 is connected to the reset inputs of all of the frequency dividers and also to the two display drivers, so that each time a breath is detected, the timing indication is cleared, all displays are returned to 00 (except sensitivity display which remains the same). Simultaneously, the system clock 132 runs directly from a oscillator 178 and its outputs are connected through an analog switch 180 and then these outputs are bridged through a capacitor 182 to a transducer 184 which outputs an audibly perceivable output indication; the audible output also is reset.

The inverted inputs into the analog switch 180 at pins 1, 3, 8 and 10 pass through the analog switch 180 and the outputs at pins 2, 4, 9 and 11 correspond to the same inputs. The inputs to pin 10 come from the system clock 132 through an inverter 186. The first input to the analog switch 180 is at pin 1. It is designated channel A, and has an input A (pin 1), an output A (pin 2) and a control lead A (pin 13). This is typical of all of the inputs, outputs and control leads of the analog switch 180, that is each switch in the analog switch 180 has an input, an output and a control lead, for a total of four inputs, four outputs and four controls. The control lead turns the analog transmission gate (in/out) either on or off. The purpose of the analog switch 180 is to provide a controllable transmission path for four frequencies or tones from the system clock 132. These tones are turned on or off sequentially (only one at a time, in sequence) by the control leads of the analog switch 180. The tones are turned on one at a time each five seconds that the clock is not reset. In other words, if a breath is not taken and the clock is not reset for fifteen seconds, for example, then three of the tones will have been audible through the piezo transducer 184 during that fifteen second interval. The first tone is 256 Hz, a low frequency, the second tone is 512 Hz, a mid frequency, the third tone is 1024 Hz, a higher frequency, and, if the fourth tone is turned on, it is a 2048 Hz, an even higher frequency. When a breath is taken, the system clock 132 is reset and the piezo transducer 184 again begins outputting an audible tone of 256 Hz for five seconds or until the next breath is taken which ever comes first.

The analog switch 180 is controlled or stepped through its tones in five second intervals by the frequency divider 176. The frequency divider 176 is controlled by the system clock 132 by the frequency divider 174. The frequency from the system clock 132 is divided into five second intervals by both of these frequency dividers 174 and 176. The frequency divider 176 turns on HI every five seconds, unless the frequency divider 176 is reset at pin 15 by a pulse. If no reset occurs, pin 4 of the frequency divider 176 turns ON at ten seconds and pin 2 of the frequency divider 176 turns OFF. Continuing with no reset, pin 7 of the frequency divider 176 turns ON at fifteen seconds and pin 4 turns OFF, at twenty seconds, pin 10 of the frequency divider 176 turns ON and pin 7 turns OFF. Pins 2, 4, 7 and 10 of the frequency divider 176 are connected to the control leads of the analog switch 180 and these turns the switch tones on as described earlier.

The purpose of the stepped tones is to provide an audible indication to the attended indicating how long it has been since a breath has been detected. Sequentially higher tones outputted from the transducer 184 indicate a longer length of time and thus a fair idea of how the subject is breathing without having to constantly monitor the visual indicators.

A selector switch 188 permits the user to select at which time interval the audible alarm indicating apnea should be heard or seen. The switch 188 for example is set at the fifteen second position on the fifteen second output of the frequency divider 176. The fixed contact of the switch 188 is connected to the set input of a flip-flop 190. If set at fifteen seconds, and pin 7 of the frequency divider 176 goes HIGH, the flip-flop 190 is set, "Q" (pin 2) goes HIGH and the alarm is set until manually reset by a switch 192.

The decoder drivers 166 and 168 each are connected to visual display 194 and 196, respectively. The visual display 194 and 196 are seven segment LED or LCD displays which provide visual output indications of the time elapsed in seconds since the last breath detected. The displays 194 and 196 are driven by the decoder drivers 166 and 168, respectively. The decoder drivers 166 and 168 are clocked by the system clock 132 to provide a sequential timing indication which is synchronized with the audible tones, that is at time interval 0 to 5 seconds as displayed by the visual displays 194 and 196 and the audible tone outputted by the transducer 184 is 256 Hz. At time intervals 6 to 10 seconds as displayed by the visual displays 194 and 196, the tone is 512 Hz, and the remaining visual display and tone correspond in a similar manner. The visual displays 194 and 196 will continue to provide or output a visually perceivable display of elasped time since the last breath detected until they are reset or until 99 seconds has lapsed, at which time they will begin counting again at 00.

A visual display 198 is another seven segment LED or LCD display. The purpose of the visual display 198 is to provide or output a visually perceivable indication of the sensitivity of detection which is selected by the user. The visual display 198 is driven by a display driver 200 which is a seven segment display driver. The seven segment display driver is controlled by an up/down counter 202. The up/down counter 202 serves a dual purpose, it not only controls the display driver 200 and thus the visual display 198, but it also controls the analog switch 114 to adjust the gain of the sense amplifier 108.

The up/down counter 202 is controlled by the user via the sensitivity select switch and one-half of the dual multivibrator 154. When the user presses the sense select switch 192, the multivibrator 154 outputs a bounce free pulse. This pulse advances the up/down counter 202 once so that the display 198 indicates "1" and the analog switch 114 channel D is turned ON. Each time the user presses the select switch 192, another pulse is generated by the multivibrator 154, the display 194 is advanced once, the up/down counter is advanced once and the gain of the sense amplifier 108 is altered. This sequence of events can occur ten times from 0 to 9 until the proper sensitivity has been selected.

It should be noted that a respiration monitoring control 30 is disclosed in Applicant's co-pending application entitled "Respiration Monitor", Ser. No. 048,896, filed May 12, 1987, and various other aspects of the respiration monitoring control circuitry 30 is disclosed in detail in Applicant's co-pending application which may be incorporated in the respiration monitoring control 30 of the present invention.

The various individual components of the respiration monitoring control 30 are commercially available from various sources. Some of the components are listed below along with a manufacturer name and model number indicating the source of these particular components.

| NUMBER | DESCRIPTION | MANUFACTURER | MODEL NO. |
| --- | --- | --- | --- |
| 100 | Phototransistor | Motorola | MFD072 |
| 108 | Sense Amplifier | Texas Instruments | TLO72 |
| 114 | Analog Switch | National Semiconductor | 4067 |
| 130 | Active Filter | National Semiconductor | MF10 |
| 154 | Multivibrator | National Semiconductor | 4538 |
| 166, 168, 200 | Decoder Driver | National Semiconductor | 4026 |
| 170, 174 | Frequency Divider | National Semiconductor | 4017 |
| 180 | Analog Switch | National Semiconductor | 4066 |
| 132 | System Clock | National Semiconductor | 4020 |
| 190 | Flip-Flop | National Semiconductor | 4043 |
| 202 | Counter | National Semiconductor | IC20 |

EMBODIMENT OF FIGURES 5 AND 6

Shown in FIGS. 5 and 6 is a modified respiration monitor 10a which includes a modified detector housing 26a.

The modified detector housing 26a includes opposite ends 300 and 302. A mirror opening 304 is formed through one end of the detector housing 26a and a mirror support 306 is slidably or movably disposed in the mirror opening 304 for movement in directions 308 and 310 within the mirror opening 304.

The mirror support 306 has opposite ends 312 and 314. One end of a modified strap 32a is disposed through an opening 316 in the mirror support 306 and the strap 32a is secured through the opening 316 to the end 314 in the mirror support 306. The end of the strap 32a may be secured to the mirror 306 by permanently connecting the end of the strap 32a to the end 314 of the mirror support 306 or the end of the strap 32a may be adjustably secured through the opening 316 to the end 314 of the mirror support 306 in a manner like that described before with respect to the end 34 of the strap 32 which is adjustably connected to the detector housing 26 by way of connecting materials 38 and 40.

The detector housing 26a includes a plate 320 which is connected to the detector housing 26a and a portion of the plate 320 extends beyond the end 302 of the detector housing 26a. An opening 322 is formed through one end of the plate 320.

The opposite end of the strap 32a is adjustably secured through the opening 322 in the plate 320 in a manner like that described before with respect to the end 34 of the strap 32 and the connecting materials 38 and 40, thereby adjustably securing the opposite end of the strap 32a generally to the end 302 of the detector housing 26a.

The respiration monitor 10a includes a sending light conductor 324 having a receiving end 326 and a sending end 328, and a receiving light conductor having a receiving end 332 and a sending end 334. The sending light conductor 324 and the receiving light conductor 330 each are constructed and adapted for conducting light between the receiving and sending ends 326 and 328 and 332 and 334, respectfully, and the sending and receiving light conductors 324 and 330, more particularly, are fiber optics with a plastic shield.

The detector housing includes a light opening 336 which extends through the end 302 of the detector housing 26a. The light opening 336 extends a distance through the detector housing 26a and intersects the mirror opening 304.

The sending end 328 of the sending light conductor 324 is insertable through the light opening 336 and into a portion of the detector housing 26a and the receiving end 332 of the receiving light conductor 330 also is insertable through the light opening 336 and extends a distance into the detector housing 26a. The detector housing 26a is adapted to receive the sending end 326 portion of the sending light conductor 24a and the receiving end 332 portion of the receiving light conductor 330 and to hold and support these portions of the sending and receiving light conductors 324 and 330 insertable therein in a position wherein the sending end 328 of the sending light conductor 324 and the receiving end 332 of the receiving light conductor 330 each are spaced a distance 338 from a mirror 340 which is secured to the end 312 of the mirror support 306. The sending end 328 of the sending light conductor and the receiving end 332 of the receiving light conductor 330 each are generally aligned and spaced the predetermined distance 338 from the mirror 340.

The sending light conductor 324 and the receiving light conductor 330 each are exited from the detector housing 26a and inserted through an opening in the strap 32a in a manner like that described before with respect to the receiving light conductor 12 and the strap 32. The sending light conductor 324 and the receiving light conductor 330 each extend a distance through the strap 32a and exit the strap 32a at a position generally between the opposite ends of the strap 32a. The receiving end 326 of the sending light conductor 324 and the sending end 334 of the receiving light conductor 330 each are connected to a modified respiration monitoring control 30a.

The respiration monitoring control 30a can be constructed exactly like the respiration monitoring control 30 described before, except the respiration monitoring control 30a includes a light source (not shown) which is disposed near the receiving end 326 of the sending light conductor 324 in a manner like that described in Applicant's co-pending application entitled, "Respiration Monitor"; Serial No. 048,896; Filed May 12, 1987. Also, the respiration monitoring control 30a could be constructed like the respiration monitoring control described in Applicant's co-pending application just mentioned.

In operation, the ends of the strap 32a are secured to the detector housing 26a in the manner described before and the straps are placed about a portion of an individual which moves in response to respiration such as the chest or abdominal area of the individual. Light is emitted from a light source and the respiration monitoring control 30a and light is received at the receiving end 326 of the sending light conductor 324 and passed or emitted from the sending end 328 of the sending light conductor 324. The light emitted from the sending light conductor 324 is reflected by the mirror 340 and the light reflected from the mirror 340 is received at the receiving end 332 of the receiving light conductor 330. The light received at the receiving end 332 of the receiving light conductor 330 is conducted by the receiving light conductor 330 therethrough and emitted or passed from the sending end 334 of the receiving light conductor 330.

As the individual inhales and exhales, the mirror support 306 is moved in either the direction 308 to decrease the distance 338 between the mirror 340 and the sending end 328 of the sending light conductor 324 and the receiving end 332 of the receiving light conductor 330, or in the direction 310 to increase the distance 338 between the mirror 340 and the sending end 328 of the sending light conductor 324 and the receiving end 332 of the receiving light conductor 330. The increasing of the distance 338 between the ends of the sending and receiving light conductors 324 and 330 and the mirror 340 results in a decrease in the intensity of light received by the receiving end 332 of the receiving light conductor 330, thereby resulting in a decreasing intensity of light received by the respiration monitoring control 30a from the sending end 334 of the receiving light conductor 330. As the individual exhales, the mirror support 306 is moved in the direction 308 thereby decreasing the distance 338 between the receiving end 332 of the receiving light conductor 330 and the mirror 340 resulting in an increase in the intensity of light received at the receiving end 332 of the receiving light conductor 330 and an increase in the intensity of light emitted from the sending end 334 of the receiving light conductor 330 and received by the respiration monitoring control 30a.

The respiration monitoring control 30a receives light from the sending end 334 of the receiving light conductor 330 and is constructed and adapted to detect respiration motion by detecting periodic increases and decreases in the intensity of light received from the sending end 334 of the receiving light conductor 330. More particularly, the respiration monitoring control 30a is constructed and adapted to provide an alarm indicating an cessation or absence of respiration motion (apnea) in response to detecting virtually no change in the intensity of light received from the sending end 334 of the receiving light conductor 330 for a predetermined period of time, such alarm signal being received by an alarm for providing perceivable output indications in response to receiving an alarm signal in the manner described before with respect to the respiration monitoring control 30a or in a manner described in Applicant's co-pending application entitled, "Respiration Monitor"; Serial No. 048,896; Filed May 12, 1987.

EMBODIMENT OF FIGURE 7

Figure 7:
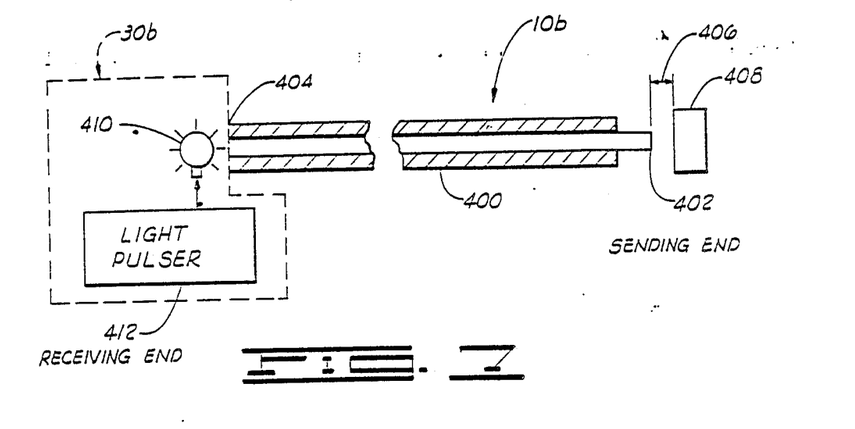
FIG. 7 is a partial sectional, partial diagrammatic view of another modified respiration monitor.

Shown in FIG. 7 is a view showing a portion of a modified respiration monitor 10b.

The respiration monitor 10b includes a light conductor 400 having sending end 402 and a receiving end 404. The sending end 402 is supported in a detector housing in a manner similar to the manner in which the light conductors are supported in the detector housing 26a shown in FIGS. 5 and 6.

The sending end 402 is spaced a distance 406 from a mirror 408. The mirror 408 is supported in the detector housing in a manner like the mirror 340 in the detector housing 26a so the distance 406 varies (increases and decreases) in response to respiration motion.

The respiration monitor 10b includes a modified respiration monitoring control 30b which includes a light source 410 connected to a light pulser 412. The light pulser 412 causes the light source 410 to output or emit a continuous appearing, but pulsed light of a predetermined frequency.

The pulsed light having the predetermined frequency outputted by the light source 410 is received at the receiving end 404 of the light conductor 400, transmitted through the light conductor 400 and emitted from the sending end 402. The light emitted from the sending end 402 is reflected from the mirror 408 and the reflected light is received at the sending end 402, transmitted through the light conductor 400 and emitted from the receiving end 404 of the light conductor 400. The light emitted from the receiving end 404 of the light conductor 400 is received by the respiration monitoring control 30b.

The respiration monitoring control 30b receives the light emitted from the receiving end 404 of the light conductor 400 and processed so the respiration monitoring control 30b output indications of respiration motion in a manner like that described before with respect to the respiration monitoring control shown in FIG. 4 or the modified respiration monitoring control shown in FIG. 10 and described below.

In the particular embodiment shown in FIG. 7, the respiration monitoring control 30b also would include an optical splinter or optical divider at the receiving end 404 of the light conductor 400. The light source 410 and the phototransistor for receiving light emitted from the receiving end 404 would be positioned with respect to the optical divider so that the optical divider operates to isolate the light source 410 from the phototransistor receiving light from the receiving end 404 of the light conductor 400. The optical divider can be a small thin piece of material positioned generally adjacent the receiving end 404 of the light conductor 400 with the light source 410 being positioned on one side of the material and the phototransistor being positioned on the opposite side of the material. In one other embodiment, the optical divider also could be a prism for directing light from the light source 410 or to the phototransistor.

EMBODIMENT OF FIGURE 8

Figure 8:
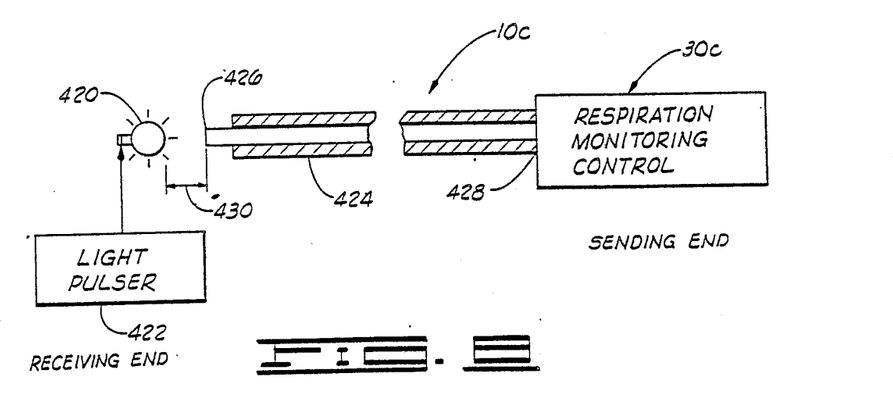
FIG. 8 is a partial sectional, partial diagrammatic view of yet another modified respiration monitor.

Shown in FIG. 8 is another modified respiration monitor 10c (partially shown) which includes a light source 420 connected to a light pulser 422. The light source 420 and the light pulser 422 are mounted in a detector housing in a manner like that shown in FIG. 1 with respect to light source 18.

The respiration monitor 10c includes a light conductor 424 having a receiving end 426 and a sending end 428. The receiving end 426 is mounted in a detector housing and spaced a distance 420 from the light source 420, in a manner like that described before in connection with the detector housing shown in FIG. 1.

The light pulser 422 caused the light source 420 emit a pulsed light having a predetermined frequency. The light outputted by the light source 420 is received at the receiving end 426 of the light conductor 424, transmitted through the light conductor 424 and emitted at the sending end 428 of the light conductor 424. The light emitted at the sending end 428 is received by a respiration monitoring control 30c which processes the received light to provide output indications of respiration motion in a manner like that described before with respect to the respiration monitoring control shown in FIG. 4 and described before or the modified respiration monitoring control shown in FIG. 10 and described below.

EMBODIMENT OF FIG. 9

Figure 9:
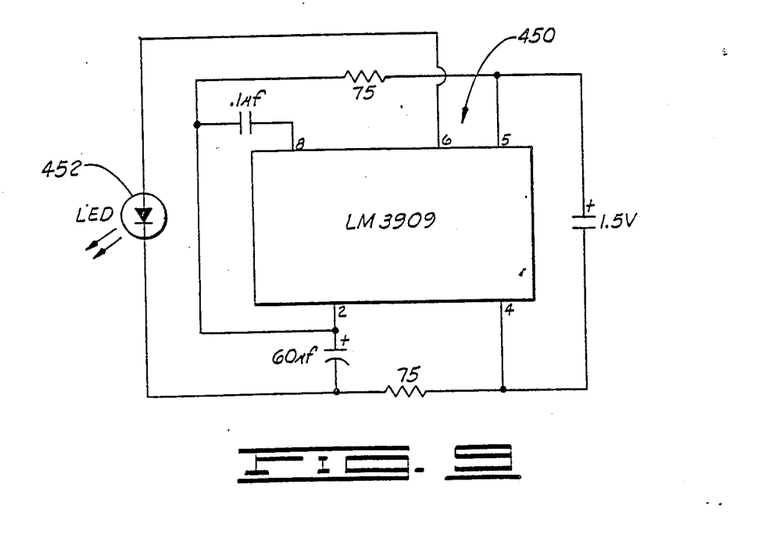
FIG. 9 is a schematic view of a light pulser which may be used in connection with the embodiments shown in FIGS. 7 and 8.

Shown in FIG. 9 is a schematic view of a light pulser 450 which is connected to a light source 452. The light pulser 450 causes the light source 452 to emit light having a predetermined frequency such as 2.0 KHz.

The light pulser 450 utilizes a commercially available circuit designated "LM3909" in FIG. 9. This particular component "LM3909" is commercially available from National Semiconductor. The light pulser 450 is suitable for use as either the light pulser 412 shown in FIG. 7 or the light pulser 422 shown in FIG. 8. The "LM3909" provides a 2 KHz rate of oscillation and provides inherent battery saving characteristics resulting in a low powered, reliable oscillator to provide frequency modulation.

EMBODIMENT OF FIG. 10

Shown in FIG. 10 is a modified respiration monitoring control 30d which may be utilized in connection with the embodiments shown in FIGS. 1-3 and 5-8. The respiration monitoring control 30d is constructed similar to the embodiment shown in FIG. 4, but the displays and some of the electronics have been eliminated including the active filter and a micropower regulator 500 "ICL7660" commercially available from Intersil has been added to supply a negative voltage source for a phototransistor 452 and an op-amp 454 (sense amplifier). All of the components in this embodiment were selected to provide a very low power and thus battery savings and a protable device of a handheld size. This particular circuit draws only 170 microamps and is powered by two "AA" alkaline batteries 506.

A voltage regulator 508 is provided for changing the 9 volt DC from a wall transformer to 3 volts DC required for use if the user decides not to use batteries.

Referring to FIG. 10, the light emitted from the light conductor is received by the phototransistor 502 and the phototransistor 502 outputs a varying DC voltage. The phototransistor 502 outputted signal is inputted into the sense amp 504 which amplifies the received signal and outputs the amplified signal which is inputted into a monostable multivibrator 510.

The multivibrator 510 is adapted to trigger on a negative going edge of the received signal and, in response to the received signal negative going edge, the multivibrator 510 outputs a HIGH signal on a signal path 512 for a predetermined duration or period of time, the period of time being about one second in the embodiment shown in FIG. 10. In other words, the multivibrator 510 is triggered "ON" and outputs a HIGH signal on the signal path 512 in response to respiration motion indicating the exhaling of the monitored individual. The HIGH signal on the signal path 512 is inputted through an OR GATE 514 which outputs a HIGH signal on the signal path 516. The HIGH signal on the signal path 516 causes a light emitting diode 518 to be lighted or, in other words, to emit light. The light emitting diode 518 will emit light for the predetermined period of time of about one second in the embodiment shown in FIG. 10 thereby indicating that a breath has been taken by the monitored individual.

The outputted HIGH on the signal path 512 also is inputted through an OR gate 520 which outputs a HIGH on a signal path 522 thereby activating a buzzer 524 which outputs an audible indication indicating that a breath has been taken.

The HIGH signal outputted on the signal path 512 also is inputted into three counters 526, 528 and 520. The HIGH outputted on the signal path 512 is inputted into the counters 526, 528 and 530 for resetting these three counters 526, 528 and 530. Thus, each time a breath is taken all three counters 526, 528 and 530 are reset. If a breath is not taken for a predetermined period of time, ten seconds in the embodiment shown in FIG. 10, then a HIGH is outputted from the counter 530 to a flip-flop 532 thereby causing the flip-flop 532 to be reset an output a HIGH on a signal path 534. The HIGH on the signal path 534 is inputted through an OR GATE 536 which outputs a HIGH on the signal path 538 thereby causing a light emitting diode 540 to emit light. Thus, when a breath is not taken for a predetermined period of time, ten seconds in the embodiment shown in FIG. 10, a HIGH is outputted on the signal path 538 thereby causing the light emitting diode 540 to emit light thereby indicating a lack of respiration for the predetermined period of time.

The flip-flop 532 output signal also is fed through a gate 541 to a buzzer 543 for providing an audible output indication indicating the absence of respiration for the predetermined period of time.

The respiration monitoring control 30d also is adapted so that it can be operated off line voltage using a wall transformer which outputs a 9 volt DC signal. The 9 volt DC signal outputted by the wall transformer is inputted into the voltage regulator 508 which outputs the three volt DC signal required for operating the various components in the respiration monitoring control 30d.

When the operating power supply is not supplied from line voltage, the respiration monitoring control 30d can be operated from the battery supply 506 in the manner described before.

The respiration monitoring control 30d also includes a LOW battery indicator 542 which is a light emitting diode. The battery supply 506 outputted power supply of 3 volts is connected through two diodes 544 and 546 and through an OR gate 548 to the light emitting diodes 542. When the battery power supply 506 outputted signal falls below a predetermined level, 2.45 volts shown in FIG. 10, a HIGH is outputted by the OR gate 504 thereby causing the light emitting diode 542 to emit light indicating that the battery supply is outputting a LOW operating voltage.

The various individual components of the respiration monitoring control 30d are commercially available from various sources. Some of the components are listed below along with a manufacturer name and model number indicating the source of these particular components.

| NUMBER | DESCRIPTION | MANUFACTURER | MODEL NO. |
|---|---|---|---|
| 500 | Voltage Convertor | Intersil | ICL7660 |
| 508 | Voltage Regulator | National Semiconductor | LM723 |
| 510 | Multivibrator | Texas Instruments | TLC555 |
| 526 | Counter | National Semiconductor | 4020 |
| 528, 530 | Counters | National Semiconductor | 4017 |
| 540 | Sense Amplifier | National | LM4250 |

| NUMBER | DESCRIPTION | MANUFACTURER | MODEL NO. |
|---|---|---|---|
| | -continued | | |
| | Semiconductor | | |

If a pulsed light signal is used in connection with the respiration monitor such as described before in connection with FIG. 8, a frequency to voltage convertor should be interposed between a capacitor 550 and the multivibrator 510 also, the capacitor shown in FIG. 10 and designated "Cl" should be changed to 0.01 microfarads. The two capacitors 550 and "Cl" act to filter the signal so that only the light signal having the predetermined frequency causes a signal to be outputted through the two capacitors and the sense amp 504 to the frequency to voltage convertor. A typical frequency to voltage convertor which may be used in this particular application is commercially available from National Semiconductor, Model LM2917.

The respiration monitors described herein also can be used to monitor motion or movement in applications other than respiration monitoring.

Shown in FIG. 11 is a modified detector housing 26d which is constructed exactly like the detector housing 26 shown in FIG. 1, except the detector housing 26d includes an enlarged light opening 50d, ribbed bar 700, a spring 702 and a collar 704.

The receiving end 14 of the receiving light conductor 12 is movably disposed in the light opening 50d in the manner described before. The collar 704 is disposed over the receiving end 14.

The spring 702 is disposed in the light opening 50d and the spring 702 biasing engages the portion of the receiving light conductor 12 in a direction 706 generally toward the ribbed bar 700. The ribbed bar 700 is disposed in the light opening 50d and ribs 708 (only one rib 708 being designated by a reference numeral in FIG. 11) on the ribbed bar 700 are sized and positioned to engage the collar 704.

The ribbed bar 700 has a plurality of spaced apart ribs 708 forming a plurality of spaced apart valleys 710 (only one valley 710 being designated by a reference numeral in FIG. 11). Each valley 710 is disposed generally between two adjacent ribs 708.

During the operation and as the receiving light conductor 12 moves back and forth in the light opening 50d, the collar 704 rides on the ribs 708 and valleys 710 thereby imparting an oscillating motion to the receiving end 14 of the receiving light conductor 12. This oscillating motion alternately brings the receiving end 14 in and out of forces with the light source 18 and imparts a pulsating signal in the receiving light conductor 12. The modified version will operate exactly like the respiration monitor 10 described before except the light conducted through the receiving light conductor 12 will be a pulsating signal. The circuit shown in FIG. 10 is adapted to receive and process this pulsating light signal in a manner exactly like that described before.

Changes may be made in the construction and operation of the various components, assemblies and parts or elements described herein or in the steps or sequence of steps of the methods described herein without departing from the spirit and scope of the invention as defined in the following claims.

I claim:

1. A respiration monitor for monitoring respiration motion of an individual, comprising:

a light source for emitting light;

a receiving light conductor having a receiving end and a sending end, the receiving light conductor being suitable for conducting light between the receiving and sending ends thereof;

means for positioning the receiving end of the receiving light conductor generally near and spaced a distance from the light source and for positioning the receiving end of the receiving light conductor and the light source near a portion of the individual which moves in response to respiration motion of the individual, and for holding the receiving end of the receiving light conductor and the light source so the distance between the receiving end of the receiving light conductor and the light source varies in response to respiration motion of the individual, the intensity of the light received by the receiving end and emitted from the sending end of the receiving light conductor being indicative of the distance between the receiving end of the receiving light conductor and the light source; and means for receiving light from the sending end of the receiving light conductor and determining indications of respiration motion in response to changes in the intensity of the received light and providing an output indication indicative of respiration motion.

2. The respiration monitor of claim 1 wherein the means for positioning and holding the receiving light conductor and the light source is defined further to include:

a detector housing having a light opening extending a distance therethrough, the light source being disposed in the detector housing near the light opening and positioned with respect to the light opening for emitting into the light opening and the receiving end of the receiving light conductor being disposed in the light opening with the light source and the receiving light conductor being positioned in the detector housing so the light source is spaced the distance from the receiving end of the receiving light conductor; and a strap assembly having the detector housing connected to a portion thereof, the strap assembly being removably attachable to the individual for removably positioning the detector housing generally near the portion of the individual which moves in response to respiration of the individual.

3. The respiration monitor of claim 2 wherein the detector housing is defined further to include a component space, and wherein the respiration monitor is defined further to include:

a battery disposed in the component space and supported in the detector housing; and means connected to the battery and to the light source having one position for establishing electrical continuity between the battery and the light source for energizing the light source thereby causing the light source to emit light, and having one other position for interrupting electrical continuity between the battery and the light source.

4. The respiration monitor of claim 2 wherein the strap assembly is defined further to include a strap having opposite ends, and wherein the detector housing is defined further to include opposite ends with the light opening extending through the one end of the detector housing and extending a distance through a portion of the detector housing, one end of the strap being adjustably connected to one end of the detector housing for varying the overall length of the strap, and wherein the strap assembly is defined further to include:

means for movably connecting one end of the strap to one end of the detector housing so that the end of the strap movably connected to the end of the detector housing is movable in response to respiration motion; and wherein the receiving light conductor is defined further as having a portion connected to the strap generally near the connection between the one end of the strap and the means for movably connecting the strap to one end of the detector housing so the receiving light conductor moves in the light opening in response to respiration motion, the distance between the receiving end of the receiving light conductor and the light source increasing as the individual inhales and the distance between the light source and the receiving end of the receiving light conductor decreasing as the individual exhales.

5. The respiration monitor of claim 4 defined further to include:

a strap bar having a portion movably connectable to one end of the detector housing and the strap bar extending a distance from the end of the detector housing defining an opening generally between a portion of the strap bar and the end of the detector housing, one end of the strap being insertable through the opening between the strap bar and the end of the housing; and wherein the strap is defined further to include means for removably connecting the end of the strap inserted through the opening between the strap bar and the end of the detector housing to a portion of the strap for securing the strap to the strap bar.

6. The respiration monitor of claim 4 wherein the means for movably connecting one end of the strap to end of the detector housing is defined further to include:

a flexible connector having one end connected to one end of the detector housing and an opposite end connected to the strap, the flexible connector being constructed such that the distance between the end of the strap and the end of the housing varies in response to respiration motion.

7. The respiration monitor of claim 6 wherein the flexible connector is defined further to encompass the space generally between the end of the strap connected thereto and the end of the detector housing connected thereto, the receiving light conductor exiting the light opening and extending through the space provided by the flexible connector and exiting the flexible connector, a portion of the receiving light conductor exiting the flexible connector being secured to the strap.

8. The respiration monitor of claim 7 wherein the end of the flexible connector connected to the housing substantially encompasses the light opening extending through the one end of the detector housing and wherein the flexible connector is defined further as being constructed of an opaque material for substantially preventing light from the exterior of the detector housing from entering into the light opening.

9. The respiration monitor of claim 1 wherein the means providing the output indication indicative of respiration motion further comprising:

means for determining an absence of respiration motion in response to determining substantially no change in the intensity of received light for a predetermined period of time and providing an output indication indicating an absence of respiration motion for the predetermined period of time.

10. The respiration monitor of claim 9 wherein the means for providing the output indication indicating an absence of respiration motion for the predetermined period of time including means for providing audible output indications having different tones with each tone being indicative of an absence of respiration motion for a predetermined period of time.

11. A method for monitoring respiration motion of an individual utilizing a light source for emitting light and a receiving light conductor having a receiving end and a sending end, the receiving light conductor being suitable for conducting light between the receiving and sending ends thereof, comprising the steps of:

positioning the receiving end of the receiving light conductor generally near and spaced a distance from the light source;

positioning the light source and the receiving end of the receiving light conductor near a portion of the individual which moves in response to respiration motion;

emitting light from the light source, varying the distance between the light source and the receiving end of the receiving light conductor in response to respiration motion so the distance between the light source and the receiving end of the receiving light conductor varies in response to respiration motion of the individual, the intensity of light received by the receiving end of the receiving light conductor varying in response to the varying distance between the light source and the receiving end of the receiving light conductor;

conducting light emitted from the light source through receiving end of the receiving light conductor, the intensity of the light received by the receiving light conductor being indicative of the distance between the light source and the receiving end of the receiving light conductor; and receiving light from the sending end of the receiving light conductor and determining indications of respiration motion in response to changes in the intensity of the light received from the sending end of the receiving light conductor.

12. A method for monitoring motion utilizing a light source for emitting light and a receiving light conductor having a receiving end and a sending end, the receiving light conductor being suitable for conducting light between the receiving and sending ends thereof, comprising the steps of:

positioning the receiving end of the receiving light conductor generally near and spaced a distance from the light source;

positioning the light source and the receiving end of the receiving light conductor near a portion which moves in response to motion;

emitting light from the light source, varying the distance between the light source and the receiving end of the receiving light conductor in response to motion so the distance between the light source and the receiving end of the receiving light conductor varies in response to motion of the individual, the intensity of light received by the receiving end of the receiving light conductor varying in response to the varying distance between the light source and the receiving end of the receiving light conductor;

conducting light emitted from the light source through receiving end of the receiving light conductor, the intensity of the light received by the receiving light conductor being indicative of the distance between the light source and the receiving end of the receiving light conductor; and receiving light from the sending end of the receiving light conductor and determining indications of motion in response to changes in the intensity of the light received from the sending end of the receiving light conductor.

* * * * *